(12) United States Patent
Kessler

(10) Patent No.: US 11,426,193 B2
(45) Date of Patent: *Aug. 30, 2022

(54) TISSUE-REMOVING CATHETER INCLUDING OPERATIONAL CONTROL MECHANISM

(71) Applicant: Covidien LP, Mansfield, MA (US)

(72) Inventor: Jason Kessler, Minneapolis, MN (US)

(73) Assignee: COVIDIEN LP, Mansfield, MA (US)

( * ) Notice: Subject to any disclaimer, the term of this patent is extended or adjusted under 35 U.S.C. 154(b) by 592 days.

This patent is subject to a terminal disclaimer.

(21) Appl. No.: 16/262,268

(22) Filed: Jan. 30, 2019

(65) Prior Publication Data

US 2019/0159802 A1 May 30, 2019

Related U.S. Application Data

(63) Continuation of application No. 14/751,369, filed on Jun. 26, 2015, now Pat. No. 10,226,276.

(51) Int. Cl.
*A61B 17/3207* (2006.01)
*A61B 17/22* (2006.01)
(Continued)

(52) U.S. Cl.
CPC .............. *A61B 17/320758* (2013.01); *A61B 17/22031* (2013.01); *A61B 17/320783* (2013.01);
(Continued)

(58) Field of Classification Search
None
See application file for complete search history.

(56) References Cited

U.S. PATENT DOCUMENTS

| 5,899,915 A | 5/1999 | Saadat |
| 6,038,475 A | 3/2000 | Sikorski et al. |

(Continued)

FOREIGN PATENT DOCUMENTS

| EP | 0515332 B1 | 2/1996 |
| EP | 2712559 A2 | 4/2014 |

(Continued)

OTHER PUBLICATIONS

International Search Report and Written Opinion for PCT Application No. PCT/US2016/039543, dated Aug. 18, 2016, pp. 13.

*Primary Examiner* — Shaun L David
(74) *Attorney, Agent, or Firm* — Stinson LLP

(57) ABSTRACT

A tissue-removing catheter for removing tissue from a body lumen during a cutting operation includes an elongate catheter body configured for insertion into the body lumen and a tissue-removing element. A motor is operably connected to the tissue-removing element for rotating the tissue-removing element. A sensor is configured to detect a parameter of the catheter body during the cutting operation. A motor control circuit is in electrical communication with the sensor and the motor. During an operational control function, the motor control circuit is configured to receive a signal from the sensor based at least in part on the detected parameter, determine whether the received signal is indicative of inefficient movement of the tissue-removing element, and adjust a rotational speed of the tissue-removing element to increase efficiency of the tissue-removing element if the received signal is indicative of inefficient movement of the tissue-removing element.

18 Claims, 18 Drawing Sheets

(51) Int. Cl.
    *A61B 17/00*     (2006.01)
    *A61B 17/32*     (2006.01)

(52) U.S. Cl.
    CPC ........... *A61B 2017/0019* (2013.01); *A61B 2017/00022* (2013.01); *A61B 2017/00075* (2013.01); *A61B 2017/00119* (2013.01); *A61B 2017/22001* (2013.01); *A61B 2017/22038* (2013.01); *A61B 2017/22051* (2013.01); *A61B 2017/22067* (2013.01); *A61B 2017/320064* (2013.01); *A61B 2017/320766* (2013.01); *A61B 2017/320791* (2013.01)

(56) References Cited

U.S. PATENT DOCUMENTS

| | | | |
|---|---|---|---|
| 6,086,544 A * | 7/2000 | Hibner | A61B 10/0275 600/564 |
| 6,245,084 B1 | 6/2001 | Mark | |
| 7,175,605 B2 | 2/2007 | Tiedtke et al. | |
| 7,931,588 B2 | 4/2011 | Sarvazyan et al. | |
| 8,033,991 B2 | 10/2011 | Sarvazyan et al. | |
| 8,150,499 B2 | 4/2012 | Gelbart et al. | |
| 8,369,921 B2 | 2/2013 | Tegg et al. | |
| 8,551,112 B2 | 10/2013 | Thornton | |
| 8,758,377 B2 | 6/2014 | Rivers et al. | |
| 2005/0149083 A1 | 7/2005 | Prudnikov et al. | |
| 2006/0074442 A1 | 4/2006 | Noriega et al. | |
| 2007/0088376 A1 | 4/2007 | Zacharias | |
| 2008/0146941 A1 | 6/2008 | Dala-Krishna | |
| 2010/0100112 A1 | 4/2010 | Kauker et al. | |
| 2011/0021926 A1 | 1/2011 | Spencer et al. | |
| 2012/0078279 A1 | 3/2012 | Mark | |
| 2012/0116391 A1 | 5/2012 | Houser et al. | |
| 2014/0100567 A1 | 4/2014 | Edwards et al. | |
| 2014/0114327 A1 | 4/2014 | Boudreaux et al. | |
| 2014/0222042 A1 | 8/2014 | Kessler et al. | |
| 2014/0277004 A1 | 8/2014 | Thatipelli | |
| 2016/0089154 A1 * | 3/2016 | Chien | A61B 17/1626 606/79 |

FOREIGN PATENT DOCUMENTS

| | | |
|---|---|---|
| EP | 2848217 A1 | 3/2015 |
| EP | 2848218 A1 | 3/2015 |
| WO | 0056230 | 9/2000 |

* cited by examiner

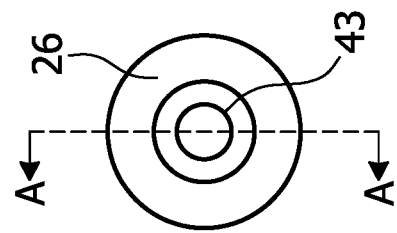
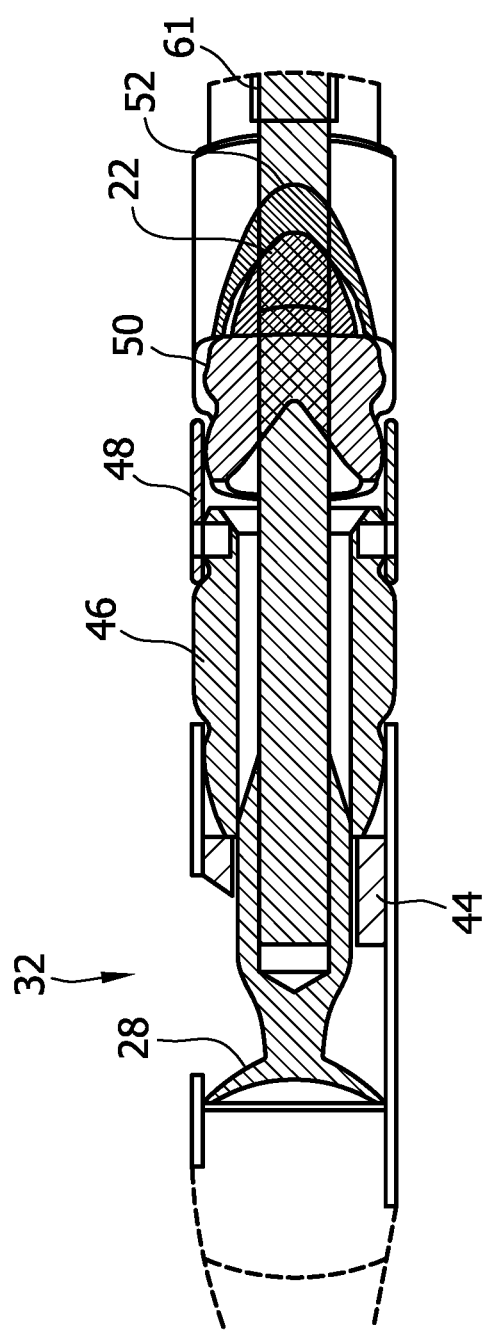
FIG. 3A
FIG. 3B

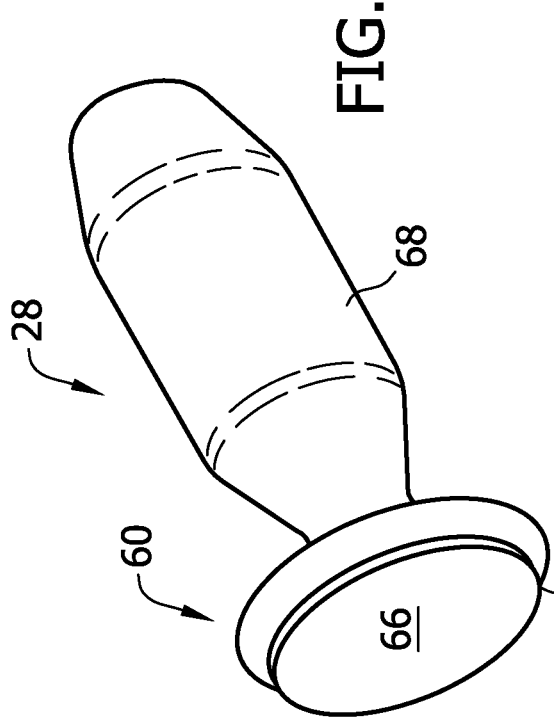
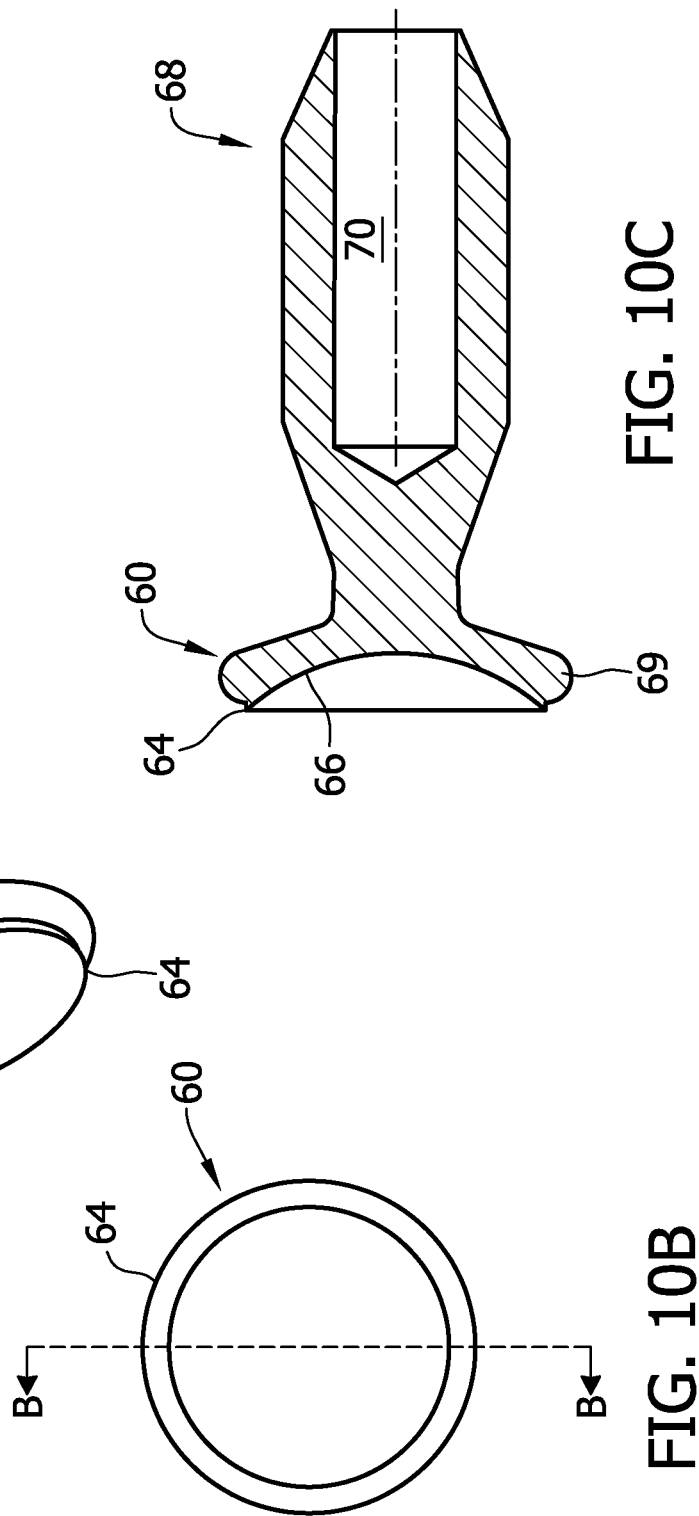
FIG. 10A
FIG. 10B
FIG. 10C

TISSUE-REMOVING CATHETER INCLUDING OPERATIONAL CONTROL MECHANISM

CROSS-REFERENCE TO RELATED APPLICATIONS

This application is a continuation of U.S. patent application Ser. No. 14/751,369, entitled TISSUE-REMOVING CATHETER INCLUDING OPERATIONAL CONTROL MECHANISM and filed on Jun. 26, 2015, which is hereby incorporated by reference in its entirety.

FIELD OF THE DISCLOSURE

Aspects of the present invention generally relate to a tissue-removing catheter for removing tissue from a body lumen including an operational control mechanism.

BACKGROUND

Vascular disease frequently arises from the accumulation of atheromatous material on the inner walls of vascular lumens, particularly arterial lumens of the peripheral and other vasculature, especially peripheral arteries, resulting in a condition known as atherosclerosis. Atherosclerosis occurs naturally as a result of aging, but may also be aggravated by factors such as diet, hypertension, heredity, vascular injury, and the like. Atheromatous deposits can have widely varying properties, with some deposits being relatively soft and others being fibrous and/or calcified. In the latter case, the deposits are frequently referred to as plaque.

Vascular disease can be treated in a variety of ways, including drugs, bypass surgery, and a variety of catheter-based approaches, including those which rely on intravascular debulking or removal of the atheromatous or other material occluding a blood vessel. A variety of methods for cutting or dislodging material and removing such material from the blood vessel have been proposed, generally being referred to as atherectomy procedures. Atherectomy catheters intended to cut or excise material from the blood vessel lumen may employ a rotatable cutting blade (or other tissue-removing element) which can be advanced into or past the occlusive material in order to cut and separate such material from the blood vessel lumen.

SUMMARY

In one aspect, a tissue-removing catheter includes a sensor configured to detect a parameter of the catheter body during the cutting operation of the catheter. A motor control circuit is in electrical communication with the sensor and a motor. During an operational control function, the motor control circuit is configured to receive a signal from the sensor based at least in part on the parameter of the catheter body detected during the cutting operation of the catheter, determine whether the received signal is indicative of inefficient movement of the tissue-removing element, and adjust a rotational speed of the tissue-removing element to increase efficiency of the tissue-removing element if the received signal is indicative of inefficient movement of the tissue-removing element. A handle for the tissue-removing catheter may include the electric motor, the sensor, and the motor control circuit.

Other features will be in part apparent and in part pointed out hereinafter.

BRIEF DESCRIPTION OF THE DRAWINGS

FIG. 3A is an end view of the distal portion of the tissue-removing catheter of FIG. 1 in which the cutter is in a closed position in the catheter body;

FIG. 3B is a sectional view along line A-A of FIG. 3A;

FIG. 10A is a perspective view of a cutter of the present invention;

FIG. 10B is an end view of the cutter of FIG. 10A;

FIG. 10C is a sectional view of the cutter along line B-B of the cutter of FIGS. 10A and 10B;

Corresponding reference characters indicate corresponding parts throughout the drawings.

DETAILED DESCRIPTION OF THE DRAWINGS

Figure 1:
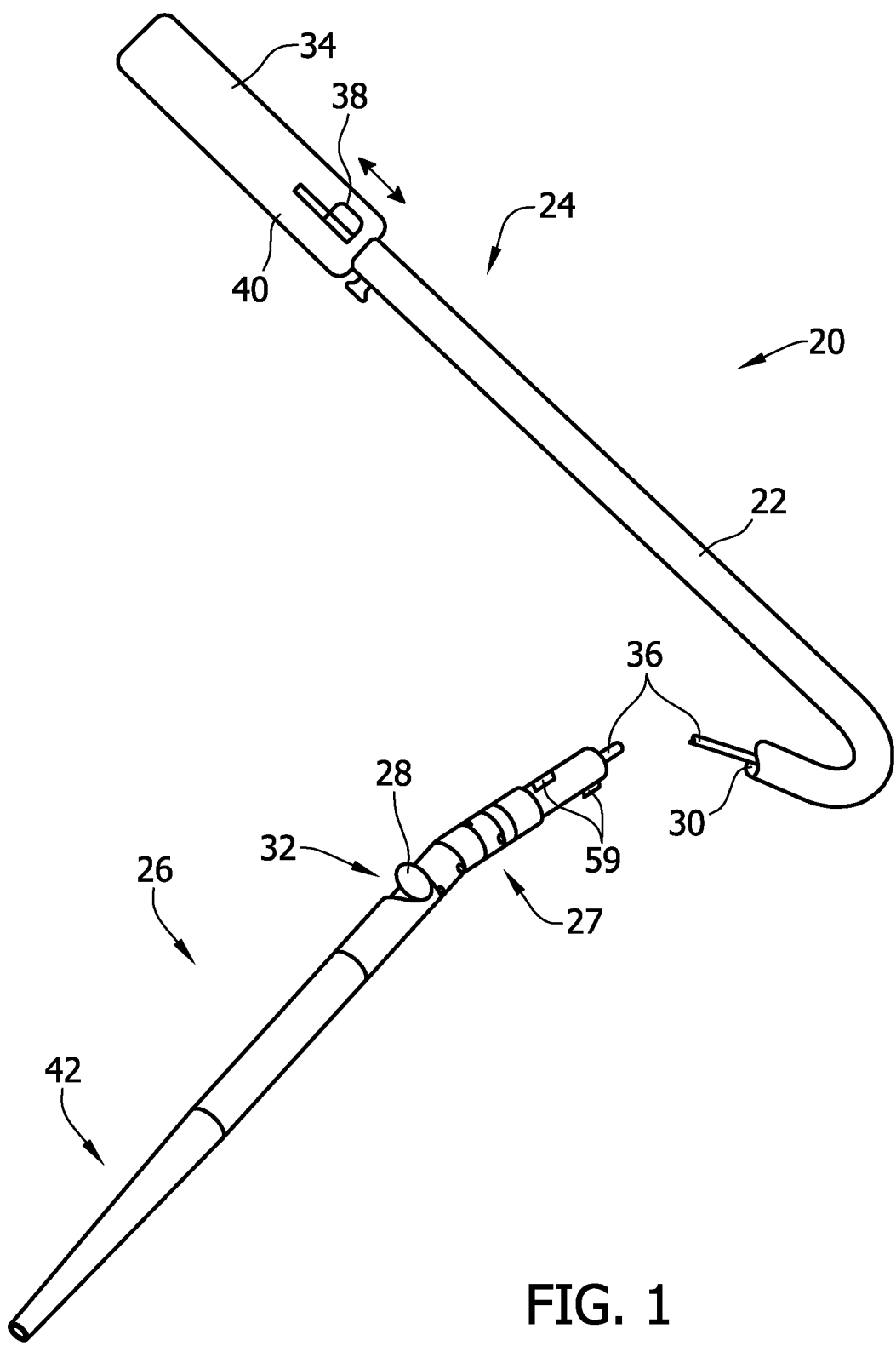
FIG. 1 is a perspective view of one embodiment of a tissue-removing catheter.

Referring now to the drawings, an operational control mechanism for a tissue-removing catheter that removes tissue from a body lumen is disclosed. In particular, embodiments of the operational control mechanism may be suitable for use with atherectomy catheters for removing (i.e., excising) an atheroma (i.e., plaque) from a blood vessel. The disclosed operational control mechanism embodiments, however, may also suitable for treating stenosis of other body lumens and other hyperplastic and neoplastic conditions in other blood vessels and body lumens, such as the ureter, the biliary duct, respiratory passages, the pancreatic duct, the lymphatic duct, and the like. Neoplastic cell growth will often occur as a result of a tumor surrounding and intruding into a body lumen. While the remaining discussion is directed toward operational control mechanisms for catheters for tissue-removing and passing through atheromatous or thrombotic occlusive material in an artery, it will be appreciated that the operational control systems may be employed with other types of catheters for removing and/or passing through a variety of occlusive, stenotic, or hyperplastic material in a variety of body lumens.

Referring now to FIG. 1, one non-limiting example of a suitable atherectomy catheter, for use with embodiments of the operational control mechanism disclosed below, is generally indicated at 20. It is understood that the operational control mechanism disclosed below may be used with other types of catheters for removing tissue from a body lumen, and is not necessarily limited to "side cutting" atherectomy and tissue-removing catheters.

The illustrated catheter 20 comprises a catheter body 22 having a proximal portion 24 and a distal portion 26. Proximal portion 24 can be coupled to distal portion 26 with a connection assembly 27 to allow pivoting or deflection of distal portion 26 relative to proximal portion 24. A tissue-removing element 28, such as a cutter, as illustrated, is disposed within a lumen 30 of the distal portion 26, whereby the distal portion can function as a cutter housing. The tissue-removing element 28 removes tissue from the lesion or obstruction. It is understood that the tissue-removing element 28 may be another type of element for removing tissue, other than the illustrated cutter, including for example, an abrasive element (e.g., a burr). The cutter 28 is typically rotatable about an axis that is parallel to the longitudinal axis of the proximal portion 24 of catheter 20 and axially movable along the longitudinal axis. The cutter 28 can access target tissue through a side opening window 32 in the distal portion 26, which is typically large enough to allow the cutter 28 to protrude through and move out of the window 32 a predetermined distance. The cutter is coupled to a handle, generally indicated at 34 (FIGS. 12-16), through a coiled drive shaft 36. Actuation of an input device or manual actuator 38 on the handle, which forms part of the deployment mechanism in this embodiment, can activate the drive shaft 36 and cutter 28, and move the cutter 28 longitudinally over a cam so as to deflect the distal portion and move the cutter 28 out of cutting window 32. As explained in more detail below, camming of the cutter 28 can cause the distal portion 26 to pivot or deflect relative to the proximal portion 24 so as to deflect and urge the cutter into the tissue in the body lumen.

In some embodiments, the distal portion 26 of the catheter may be moved to an angled or offset configuration from the longitudinal axis of the proximal portion 24 of the catheter and the cutter 28. In some embodiments, the cutter 28 can also be deflected off of the axis of the proximal and/or distal portion of the catheter. Moving the distal portion 26 to an angled/offset position may cause a portion of the catheter 20 to urge against a target tissue, may expose the cutter 28 through the window 32 or both, in various embodiments.

The proximal portion 24 of the catheter body 22 may be relatively flexible and at least a portion of the distal portion 26 may be relatively rigid. Additionally, the distal portion 26 may include a flexible distal tip member 42 at the distalmost end of the body 22. The flexible proximal portion 24 of the catheter is typically a torque shaft and the portion of the distal portion 26 defining the cutting window 32 is typically a rigid tubing. The torque shaft, which is indicated by the same reference numeral 24, facilitates transportation of the catheter body 22 and cutter 28 to the diseased site. The proximal end of the torque shaft 24 is coupled to the handle 34 and the distal end of the torque shaft is attached to the distal, rigid portion 26 of the catheter 20 through the connection assembly 27. The drive shaft 36 is movably positioned within the torque shaft 24 so as to rotate and axially move within the torque shaft 24. The drive shaft 36 and torque shaft 24 are sized to allow relative movement of each shaft without interfering with the movement of the other shaft. The catheter body 22 will have the pushability and torqueability such that torqueing and pushing of the proximal end will translate motion to the distal portion 26 of the catheter body 22.

Figure 1A:
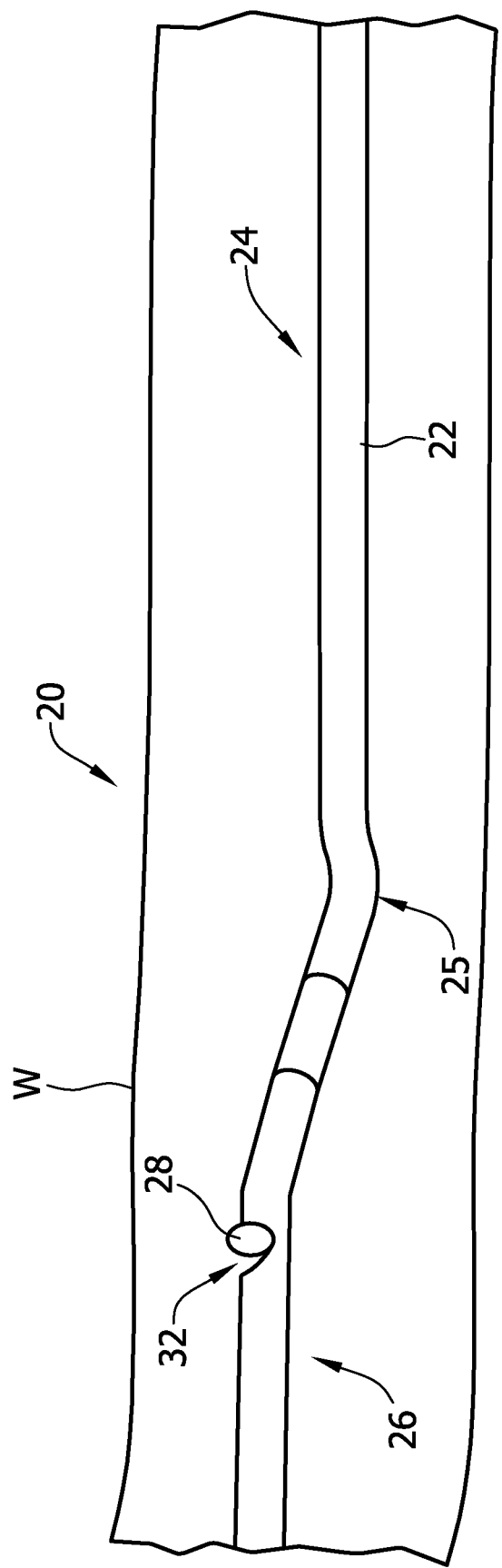
FIG. 1A is a side view of a portion of a tissue-removing catheter as in FIG. 1, where the body has a distal portion with a bend, according to one embodiment of the present invention.

Referring now to FIG. 1A, the catheter 20 as in FIG. 1 may have a flexible proximal portion 24 which additionally includes urging means 25. As shown in FIG. 1A, urging means 25 may comprise a bent or curved shape towards the distal end of proximal portion 24, which may help urge the cutter 28 or other tissue-removing element toward a wall of a body lumen to enhance treatment. Such a bend increases the working range of the catheter by allowing the cutter to be urged into a lumen wall across a wider diameter.

In other embodiments, urging means 25 may take many other suitable forms. For example, a similar result to the bend may be achieved by including a distal portion that is not permanently bent but that is more rigid on one side than on the opposite side of catheter body 22. Thus, when proximal tension is applied to the proximal portion 24, as when proximal force is applied to the tissue-removing apparatus to expose the cutter 28 through the window 32, the urging means 25 will cause the catheter body 22 to bend toward the less rigid side. The less rigid side will typically be the same side as the window 32, so that the window 32 and/or the cutter 28 will be urged against a wall of a body lumen by the bend. In still other embodiments, a shaped element may be introduced into catheter body 22 to act as urging means 25. Any suitable urging means is contemplated.

Figure 2:
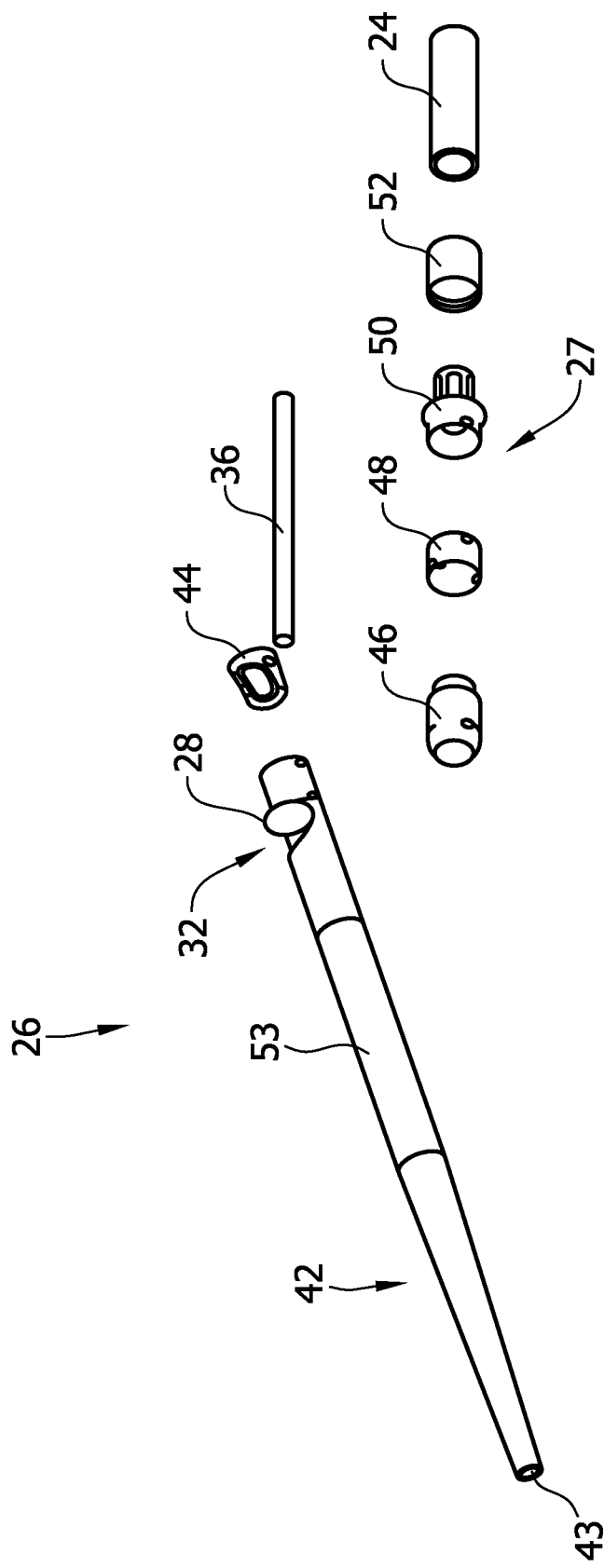
FIG. 2 is an exploded view of an exemplary distal portion of the tissue-removing catheter.

Referring to FIG. 2, the distal portion 26 may also include a collection chamber 53 for storing the severed atheromatous material disposed between the rigid portion and the distal tip 42. The distal tip member 42 can have a distal opening 43 and a distal guidewire lumen that is sized to allow an imaging guidewire or conventional guidewire (not shown) to be advanced distally through the tip member. For example, some embodiments may include a distal guidewire lumen having a length of between about 1.0 cm and about 5.0 cm, and preferably between about 2.0 cm and about 3.0 cm. Such a distal guidewire lumen may be used alone or in conjunction with a proximal guidewire lumen located on another, more proximal, portion of the catheter 20.

A ramp or cam 44 can at least partially fit within the distal portion 26 of the catheter 20. As will be described in detail below, in many embodiments proximal movement of the cutter 28 over the ramp 44, causes the deflection of the distal housing 26 and guides cutter out of cutting window 32. Attached to the ramp 44 is a housing adaptor 46 that can connect one or more articulation members 48 to the distal tip member 42 to create an axis of rotation of the distal portion 26. The housing adaptor 46 and articulation member 48 allow the distal portion 26 of the catheter 20 to pivot and bias against the body lumen. In the illustrated embodiment there are only one housing adaptor 46 and one articulation member 48, but it should be appreciated that the catheters of the present invention can include, two, three, or more joints (e.g., axis of rotation), if desired. Moreover, the axes of rotation can be parallel or non-parallel with each other.

The catheter 20 can also include a shaft adaptor 50 and collar 52 to couple articulation members 48 to the torque shaft 22. Shaft adaptor 50 can connect the housing to the torque shaft 22 and the collar 52 can be placed over a proximal end of the shaft adaptor and crimped for a secure attachment. It should be appreciated by one of ordinary skill in the art that while one catheter embodiment has the above components that other catheters may include more or fewer of the components described above. For example, some components can be made integral with other components and some components may be left out entirely. Thus, instead of having a separate ramp 44, the ramp may be integrated with the distal portion 26 to direct the cutter 28 out of the cutting window 32.

As shown in FIGS. 3-5, the cutter 28 will generally be movable between two or more positions using a deployment mechanism. In the illustrated embodiment, the actuator 38 actuates operation of the deployment mechanism, although in other embodiment, the deployment mechanism may be actuated by other actuators. In the illustrated embodiment, the deployment mechanism allows for the cutter 28 to be selectively moveable to a stowed or neutral position (FIGS. 3A and 3B) in which the cutter is stowed in the distal portion 26 of the catheter body 22 and is not exposed through the window 32. In some embodiments, an imaging device (not shown) can be coupled to cutter 28 so as to image the body lumen through cutting window 32 when cutter is in the neutral position. Once the catheter 20 has reached the target site, the cutter 28 can be moved proximally to a tissue-removing position (FIGS. 4A and 4B), in which the cutter 28 extends through the cutting window 32 a distance L1 beyond an outer diameter D of the distal portion 26. In some embodiments, in the tissue-removing position, the cutter 28 will have deflected the distal portion 26 and the cutter's axis of rotation will generally be in line with connection assembly 27 but angled or offset from longitudinal axis of the distal portion of the catheter body 22.

Figure 5A:
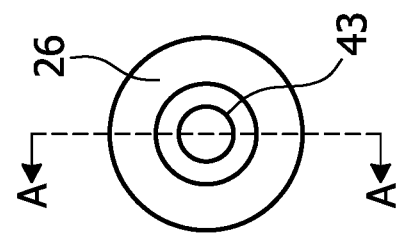
FIG. 5A is an end view of the distal portion of the tissue-removing catheter of FIG. 1 in which the cutter is in a packing position within a tip member of the catheter.
Figure 5B:
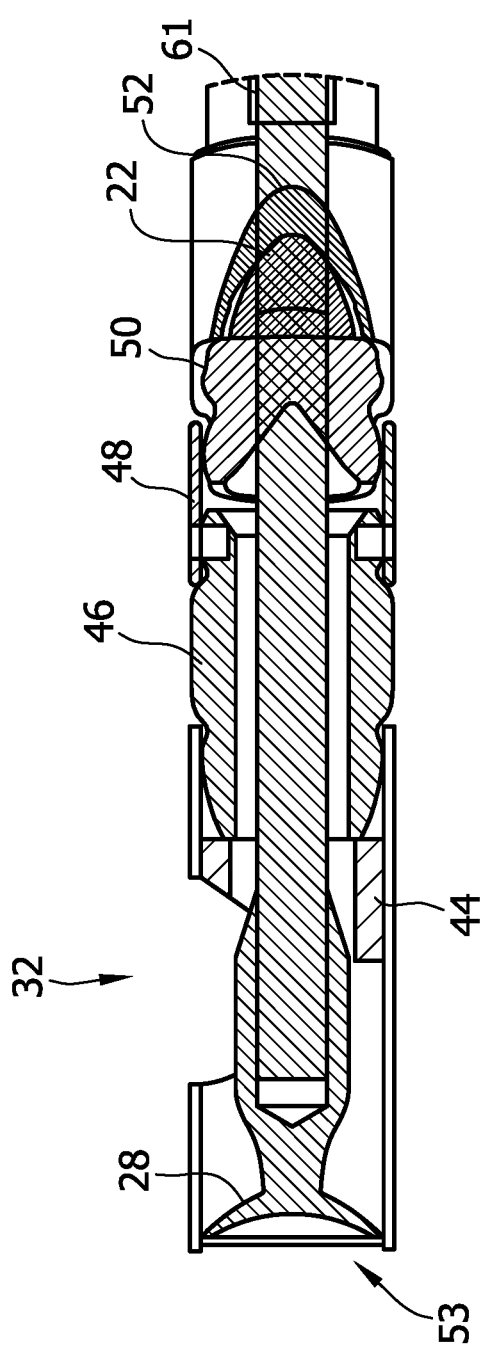
FIG. 5B is a sectional view along line A-A of FIG. 5A.

Optionally, in some embodiments, the cutter 28 can be moved to a packing position, in which the cutter is moved distally, beyond the stowed or neutral position, so as to pack the severed tissue into the distal collection chamber 53 (FIGS. 5A and 5B). It should be appreciated however, that while the exemplary embodiment moves the cutter 28 to the above described positions, in other embodiments the cutter can be positioned in other relative positions. For example, instead of having the neutral position distal of the cutting window, the neutral position may be proximal of the window, and the open position may be along the distal end of the cutting window, or the like.

Figure 3C:
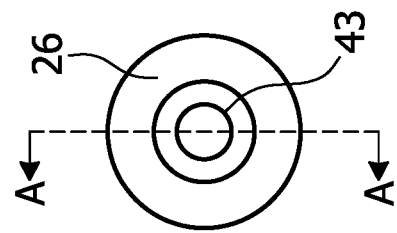
FIGS. 3C and 3D are views of the distal portion of a tissue-removing catheter, where the distal portion has a locking shuttle mechanism.

Referring again to FIGS. 4A and 4B, the interaction of the components of the rigid distal portions 26 in one exemplary embodiment will be further described. As shown in FIG. 4B, the cutting window 32 is typically a cutout opening in the distal portion 26. While the size of the cutting window 32 can vary, the cutting window should be long enough to collect tissue and circumferentially wide enough to allow the cutter 28 to move out of the cutting window during cutting, but sized and shaped to not expel emboli into the vasculature. The cams or ramp 44 (shown most clearly in FIG. 4B) can be disposed in the distal portion 26 of the catheter body 22 to guide or otherwise pivot the cutter 28 out of the cutting window 32, from the non-exposed, neutral position (FIG. 3B) to the exposed, tissue-removing position (FIG. 4B) as the cutter 28 is pulled proximally through tensioning of drive shaft 36 via the actuator 38. This operation is explained in detail below.

Figure 4A:
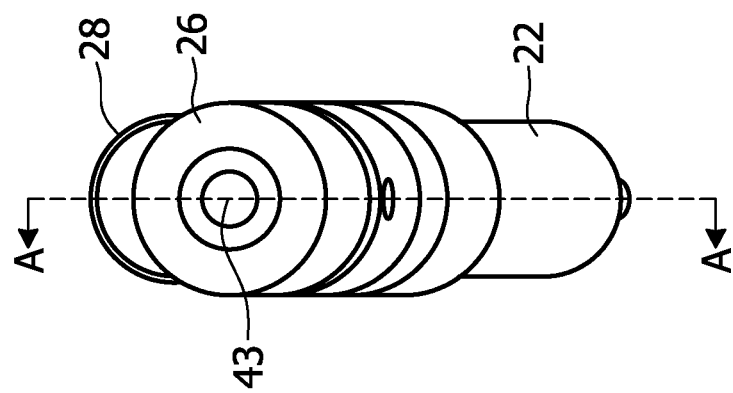
FIG. 4A is an end view of the distal portion of the tissue-removing catheter of FIG. 1 in which the cutter is in an open position outside of the cutting window.
Figure 4B:
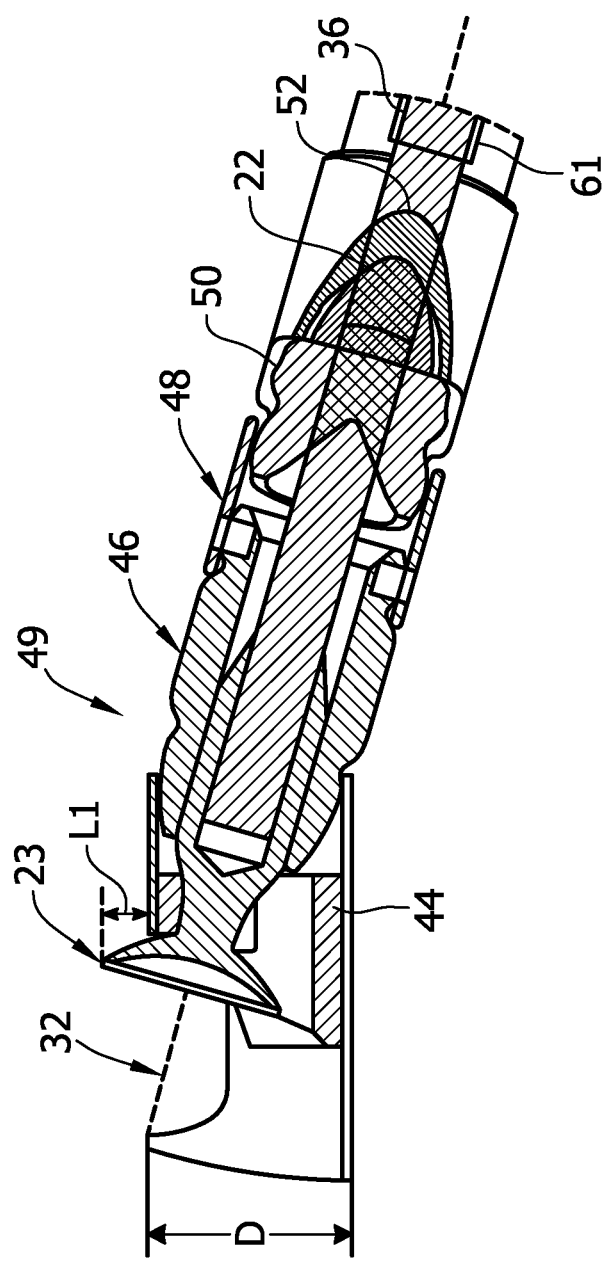
FIG. 4B is a sectional view along line A-A of FIG. 4A.

Referring to FIGS. 4A and 4B, a joint 49 is located proximal to the cutting window 32 to provide a pivot point for camming of the distal portion 26 relative to the proximal portion 24. The bending at the joint 49 is caused by the interaction of the cams or ramps 44 with cutter 28 and the tensile force provided through drive shaft 36. In the exemplary configuration, the joint 49 includes a housing adaptor 46 that is pivotally coupled to the distal rigid portion 26. As shown in FIGS. 4A and 4B, the resulting pivoting of the rigid distal portion 26 relative to the proximal portion 24 causes a camming effect which urges the distal portion against the body lumen wall without the use of urging means (e.g., a balloon) that is positioned opposite of the cutting window 32. Thus, the overall cross sectional size of the catheter body 22 can be reduced to allow the catheter 20 to access lesions in smaller body lumens. In exemplary embodiments, the distal portion 26 can deflect off of the axis of the proximal portion 24 of the catheter 20 typically between 0° degrees and 30° degrees, usually between 5° degrees and 20° degrees, and most preferably between 5° degrees and 10° degrees. The angle of deflection relates directly to the urge. Urge, however, does not necessarily relate to force but more to the overall profile of the catheter 20. For example, the greater the angle of deflection, the larger the profile and the bigger the lumen that can be treated. The ranges were chosen to allow treatment of vessels ranging from less than 2 mm to greater than 3 mm within the limits of mechanical design of the components. It should be appreciated however, that the angles of deflection will vary depending on the size of the body lumen being treated, the size of the catheter, and the like.

In some embodiments, the deflection of the distal portion 26 of the catheter 20 urges the cutter 28 into the exposed, tissue-removing position (FIG. 4B), such that distal advancement of the entire catheter body 22 can move the rotating cutter through the occlusive material. Because the cutter 28 is moved a distance L1 beyond the outer diameter of the distal portion 26 of the catheter 20 and outside of the cutting window 32, the user does not have to invaginate the tissue into the cutting window. In some embodiments, for example, the cutter 28 can be moved between about 0.025 mm and about 1.016 mm, and preferably between about 0.025 mm and about 0.64 mm, beyond the outer dimension of the distal portion 26. It should be appreciated that the cutter excursion directly relates to the depth of cut. The higher the cutter 28 moves out of the cutting window 32 the deeper the cut. The ranges are chosen around efficacy without risk of perforation of the body lumen.

Figure 3D:
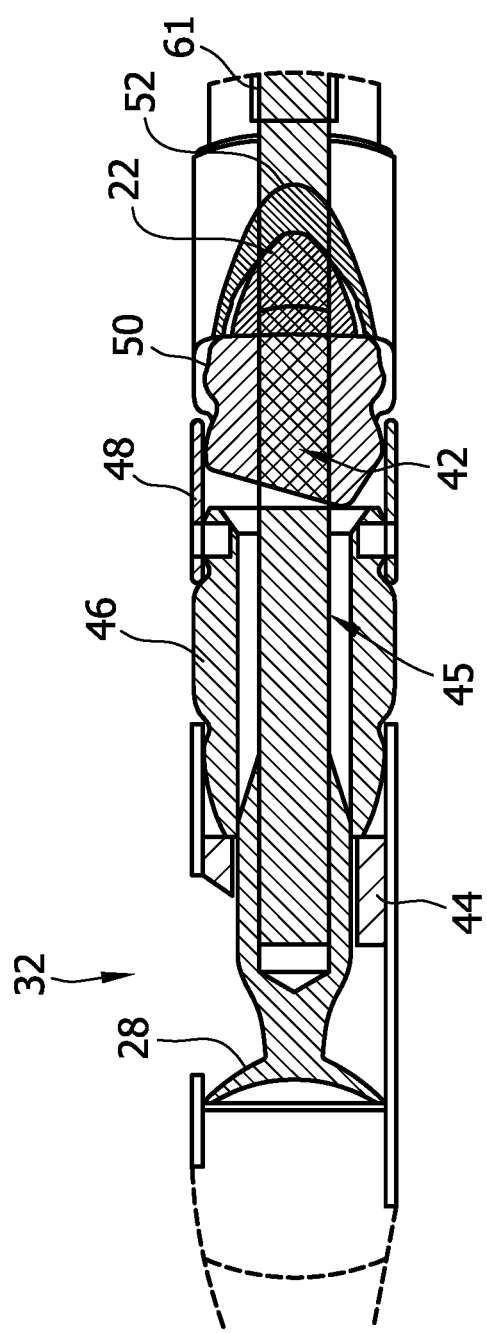
Figure 4C:
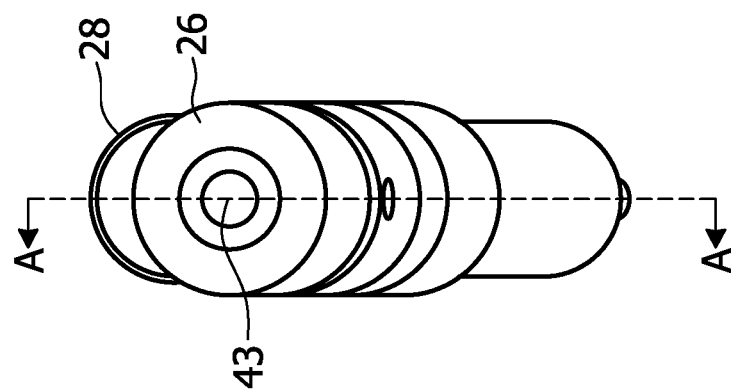
FIGS. 4C and 4D are views of the distal portion of a tissue-removing catheter, where the distal portion has a locking shuttle mechanism.
Figure 4D:
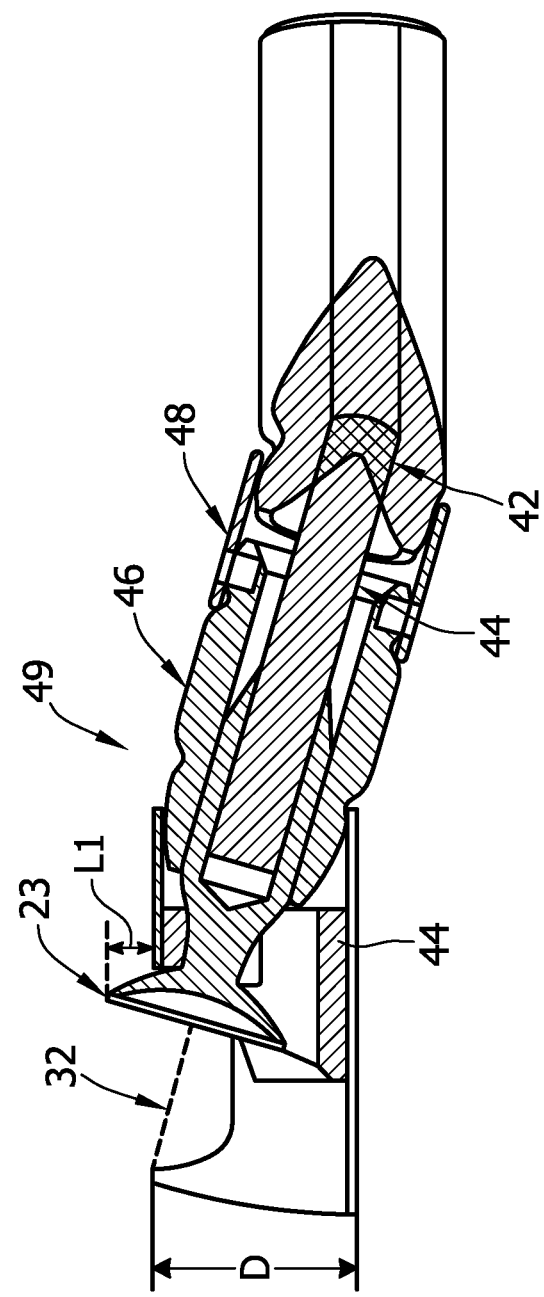

Some embodiments of the catheter 20 include a shuttle mechanism or other similar mechanism for temporarily locking the catheter in the tissue-removing position. FIGS. 3C and 3D illustrate such an embodiment in the neutral, non-tissue-removing position. Such embodiments generally include a shuttle member 45 and a shuttle stop member 42. The shuttle stop member 42 is typically disposed at an angle, relative to a longitudinal axis through the catheter. FIGS. 4C and 4D show the same embodiment in the tissue-removing position. When the cutter 28 is moved into the tissue-removing position in such embodiments, the shuttle member 45 falls into the shuttle stop member 42 and thus locks the cutter 28 in the tissue-removing position. To unlock the cutter 28, the cutter may be advanced forward, distally, to release the shuttle member 45 from the shuttle stop member 42.

Some embodiments including a shuttle mechanism will also include two joints in the catheter body 22. Thus, catheter body 22 will include the distal portion 26, the proximal portion 24 and a middle portion. When shuttle mechanism is activated to expose cutter 28 through window 32, the middle portion may orient itself at an angle, relative to the proximal and distal portions, thus allowing cutter to be urged towards a side of a lumen. Such a two-jointed configuration may provide enhanced performance of the catheter 20 by providing enhanced contact of the cutter 28 with material to be debulked form a body lumen.

Pushing the entire catheter 20 across a lesion removes all or a portion of the lesion from the body lumen. Severed tissue from the lesion is collected by directing the removed tissue into the collection chamber 53 in the tip member 42 via the cutter 28. Once the catheter 20 and cutter 28 have moved through the lesion, the cutter can be advanced distally to "part off position" the lesion. During "parting off", the cutter 28 is moved distally from the tissue-removing position back into the cutting window 32 (FIG. 3B) and to its neutral or stowed position. The collection chamber 53 of the tip member 42 acts as a receptacle for the severed material, to prevent the severed occlusive material from entering the body lumen and possibly causing downstream occlusions. After "parting off", the cutter 28 can be moved distally to a packing position, in which the cutter moves distally within the collection chamber 53 to pack the severed tissue into collection chamber 53 (FIG. 3B). Typically, the collection chamber 53 will be large enough to allow multiple cuts to be collected before the catheter 20 has to be removed from the body lumen. When the collection chamber 53 is full, or at the user's discretion, the catheter 20 can be removed, emptied and reinserted over the guidewire.

Figure 6:
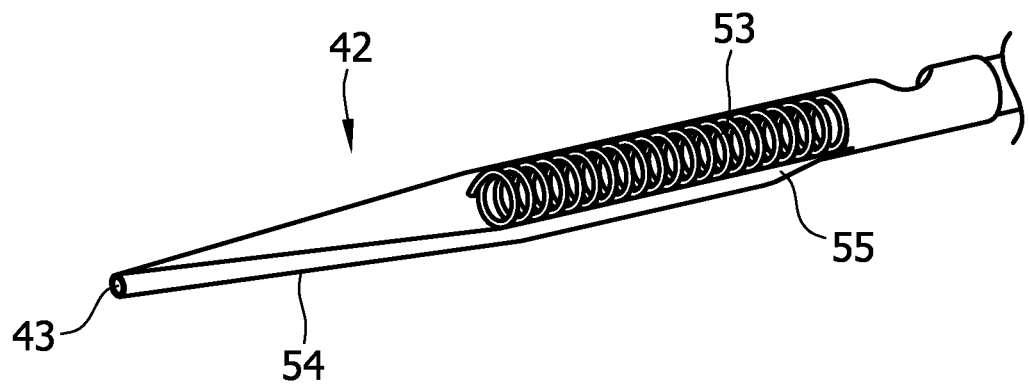
FIGS. 6 to 8 illustrate a monorail delivery system of the present invention.
Figure 7:
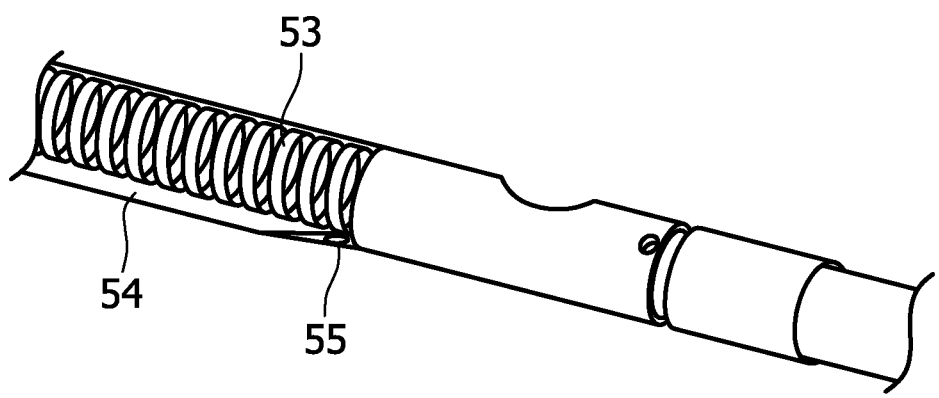
Figure 8:
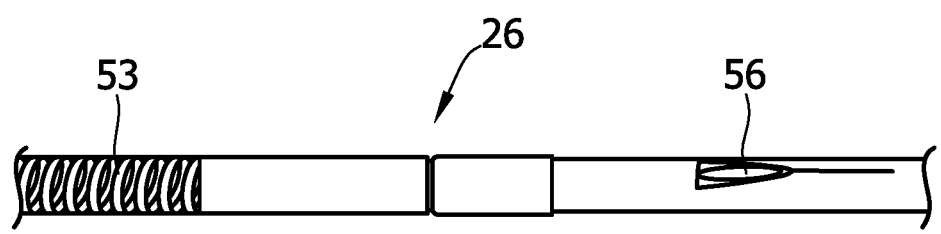
Figure 9C:
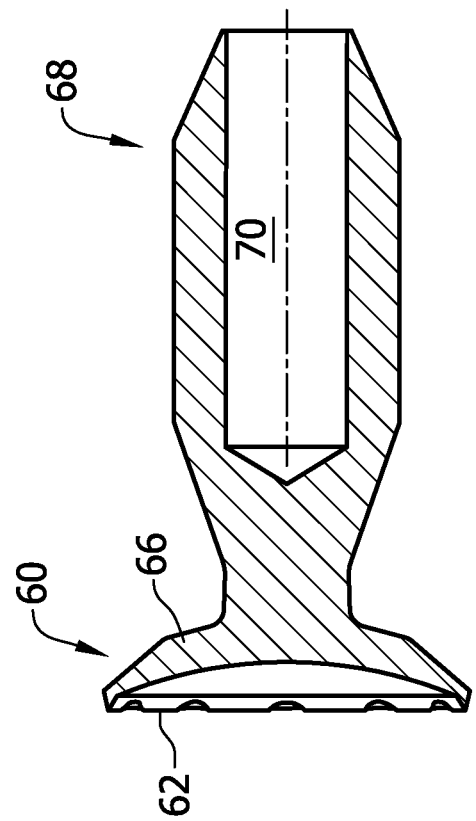
FIG. 9C is a sectional view of the cutter along line A-A of the cutter of FIGS. 9A and 9B.
Figure 9A:
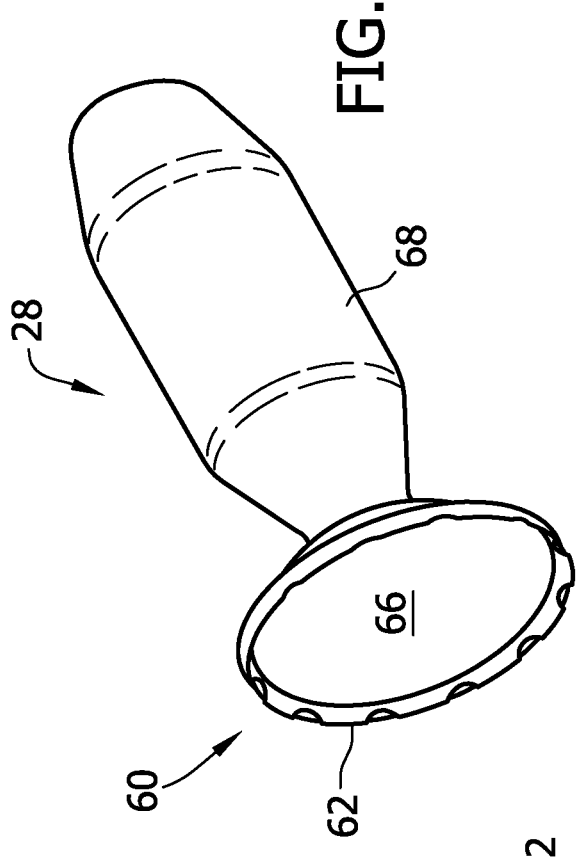
FIG. 9A is a perspective view of a cutter of the present invention.
Figure 9B:
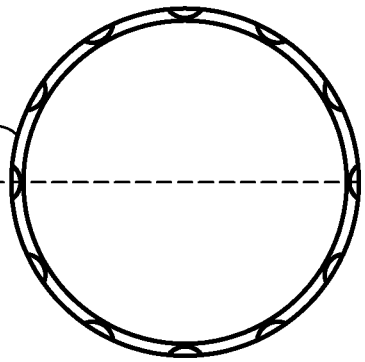
FIG. 9B is an end view of the cutter of FIG. 9A.

FIGS. 6 through 8 illustrate one exemplary monorail delivery system to assist in positioning the cutter 28 at the target site. For example, tip member 42 of the catheter can include a lumen 54 having a distal opening 43 and a proximal opening 55 that is sized to receive a guidewire, having a diameter of about 0.014 in., about 0.018 in., about 0.032 in. or any other suitable diameter.

The catheters 20 can include radiopaque markers so as to allow the user to track the position of the catheter under fluoroscopy. For example, as already described, a point or area around or adjacent to the window 32 may be made radiopaque. In other embodiments, the distal portion 26 can be radiopaque and radiopaque markers can be disposed on the flexible shaft 36. Typically, the markers 59 will be disposed along the top, proximal to the cutting window 32, and on the bottom of the catheter 20 to let the user know the position of the cutter and cutting window relative to the target site. If desired, the top and bottom markers 59 can be different shaped so as to inform the user of the relative orientation of the catheter 20 in the body lumen. Because the guidewire will form a helix in its transition from lumen 56 to tip member lumen 54, the user will be able to view the top and bottom radiopaque markers 59 without interference from the guidewire. Some embodiments of the catheter 20 can also include a radiopaque cutter stop 61 (FIG. 3B) that is crimped to driveshaft 36 proximal of the cutter that moves with the cutter so as to let the user know when the cutter 28 is in the open position.

FIGS. 9A through 11D show some exemplary embodiments of the cutter 28. The distal portion 60 of the rotatable cutter 28 can include a serrated knife edge 62 or a smooth knife edge 64 and a curved or scooped distal surface 66. The distal portion 60 may have any suitable diameter or height. In some embodiments, for example, the diameter across the distal portion 60 may be between about 0.1 cm and about 0.2 cm. A proximal portion 68 of the cutter 28 can include a channel 70 that can be coupled to the drive shaft 36 that rotates the cutter. As shown in FIGS. 10A-10C, some embodiments of the cutters 28 can include a bulge or bump 69 that is provided to interact with a stent so as to reduce the interaction of the cutting edge with the stent. In any of the foregoing embodiments, it may be advantageous to construct a serrated knife edge 62, a smooth knife edge 64, or a scooped distal surface 66 out of tungsten carbide.

Figure 11A:
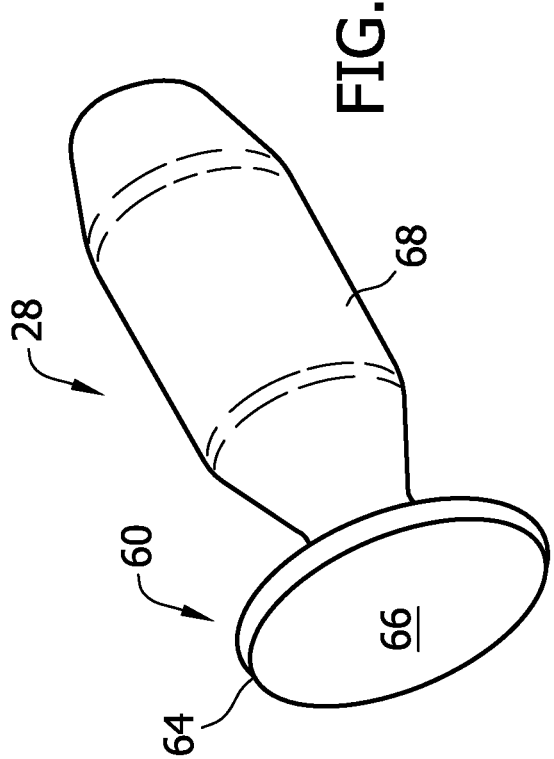
FIG. 11A is a perspective view of another cutter of the present invention.
Figure 11C:
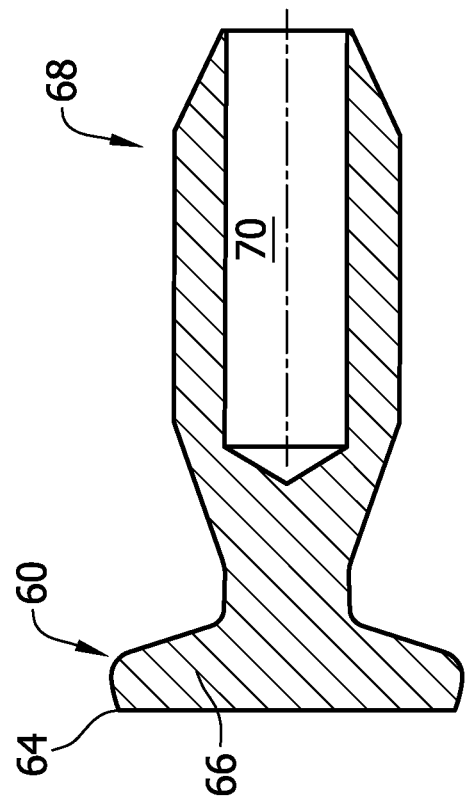
FIG. 11C is a sectional view of the cutter along line C-C of the cutter of FIGS. 11A and 11B.
Figure 11B:
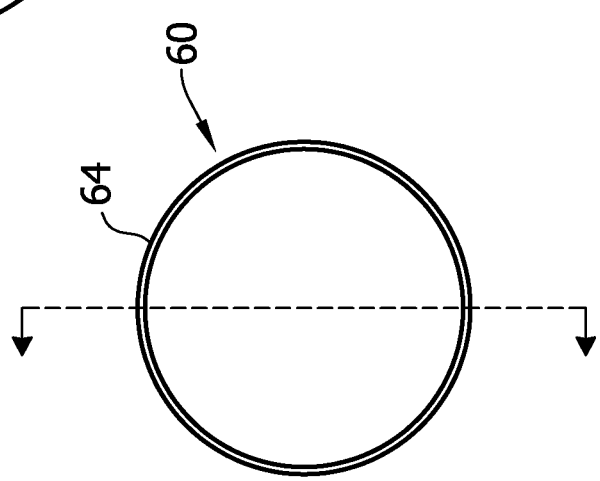
FIG. 11B is an end view of the cutter of FIG. 11A.
Figure 11D:
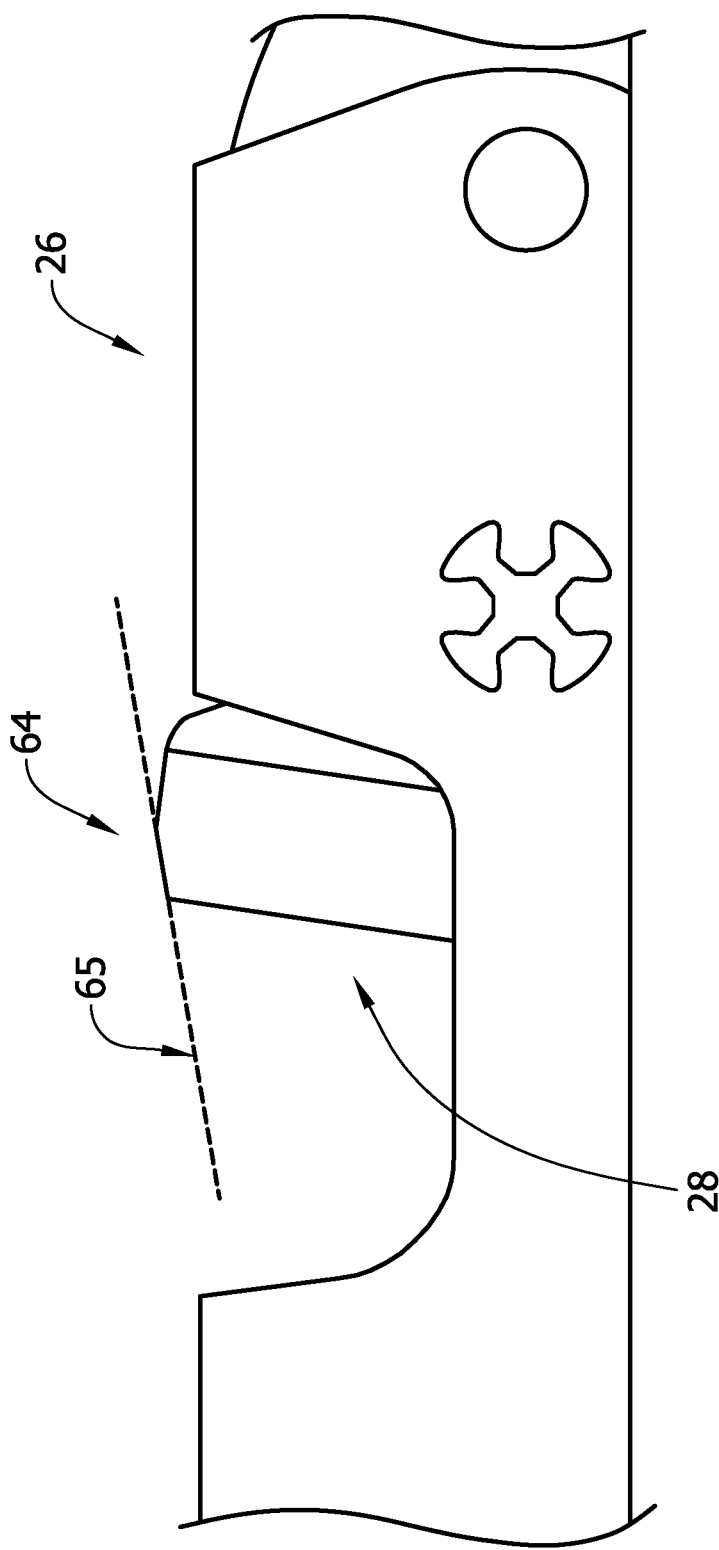
FIG. 11D is a side view of another embodiment of a cutter, shown partially within a catheter body.
Figure 12:
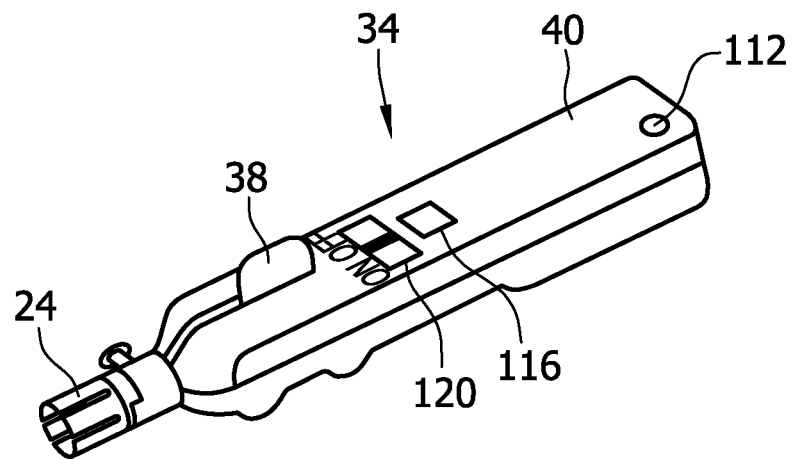
FIG. 12 is a perspective view of an embodiment of a handle for the tissue-removing catheter, including an embodiment of an operational control mechanism.
Figure 13:
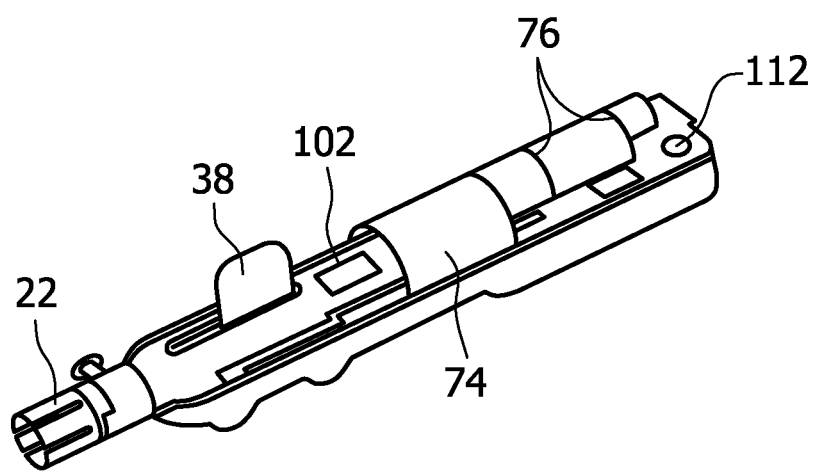
FIG. 13 is similar to FIG. 12 with a cover of the handle removed.
Figure 14:
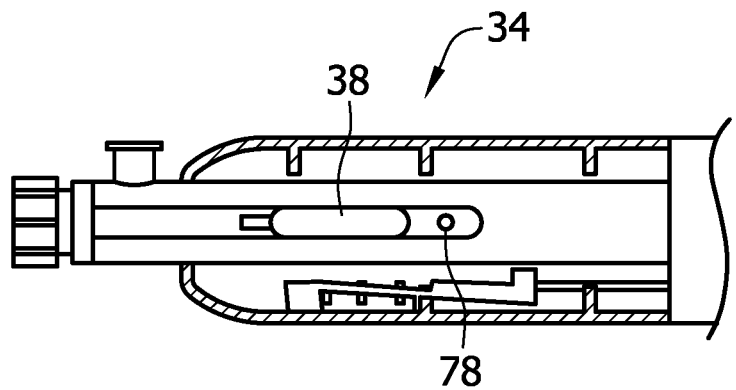
FIG. 14 illustrates a neutral position of a lever of the handle.
Figure 15:
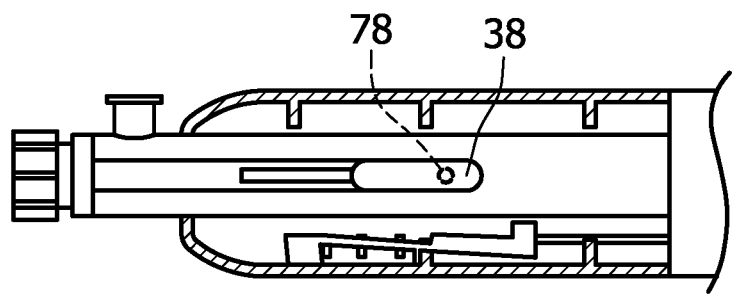
FIG. 15 illustrates a tissue-removing position of the lever of the handle.
Figure 16:
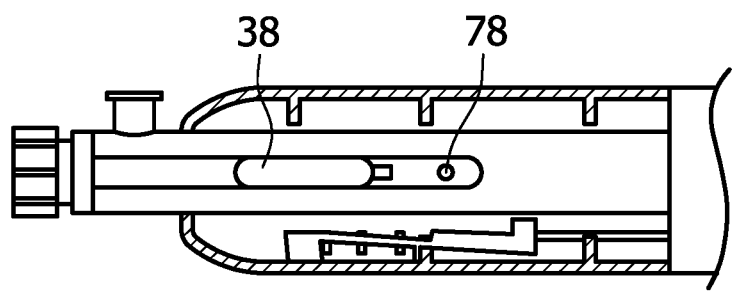
FIG. 16 illustrates a packing position of the lever of the handle.

Another embodiment of a cutter 28 shown in side view within a distal portion 26 in FIG. 11D. In this embodiment, the cutter 28 has a beveled edge 64, made of tungsten carbide, stainless steel, titanium or any other suitable material. The beveled edge 64 is angled inward, toward the axis of rotation (or center) of the cutter 28, creating a "negative angle of attack" 65 for the cutter 28. Such a negative angle of attack may be advantageous in many settings, when one or more layers of material are desired to be debulked from a body lumen without damaging underlying layers of tissue. Occlusive material to be removed from a vessel typically has low compliance and the media of the vessel (ideally to be preserved) has higher compliance. A cutter 28 having a negative angle of attack may be employed to efficiently cut through material of low compliance, while not cutting through media of high compliance, by allowing the high-compliance to stretch over the beveled surface of cutter.

Referring to FIGS. 12 through 16, one embodiment of the handle 34 will now be described in detail. The handle 34 includes a housing 40 that is sized and shaped to be held in a hand of the user. An electric motor 74 (e.g., a DC motor) is contained in the housing 40, along with a power source 76 (e.g., a battery or other source of DC power) electrically connected to the motor for powering the motor. The drive shaft 36 is operatively coupled to the motor 74 when the catheter 20 is connected to the handle 34 for driving rotation of the drive shaft and the cutter 28. In some embodiments, at maximum power the motor 74 can rotate drive shaft 36 between 1,000 rpm and 15,000 rpm or more, if desired. The manual actuator 38 (e.g., a lever, as illustrated) on the exterior of the housing 40 allows the user to control operations of the catheter 20. For example, in the illustrated embodiment the lever 38 is axially moveable relative to the housing 40. In particular, the lever 38 is movable to a neutral position (shown in FIG. 14), whereby the cutter 28 is in its non-exposed, neutral position (FIG. 3D). To expose the cutter 28 and activate the motor 74 to drive rotation of the cutter, the lever 38 is moved proximally from the neutral position to a proximal, tissue-removing position of the lever (see FIG. 15) to move the cutter proximally and out of cutting window 32 (FIG. 4B) to its tissue-removing position and simultaneously activate the motor 74. For example, proximal movement of the lever 38 to the proximal position may actuate (e.g., depress) an electrical switch 78 that electrically connects the power source 76 to the motor 74. To part off tissue, the lever 38 is moved distally from the proximal, tissue-removing position, back to its neutral position (FIG. 14) to drive (i.e., move) the cutter 28 distally into the distal portion of the catheter 20 (FIG. 3D). As the lever 38 is positioned in its neutral position, the electrical switch 78 is released (i.e., opened) so as to deactivate the electric motor 74. To pack the removed tissue in the collection chamber 53 of the distal tip member 42, the lever 38 is moved distally from the neutral position to a distal position, packing position of the lever (see FIG. 16) to drive (i.e., move) the cutter 28 distally into the collection chamber and to its packing position (FIG. 5B). It should be appreciated, while the figures illustrate the use of an lever 38 or thumb switch, other embodiments of the present invention can use other types of actuators, such as separate buttons (e.g., a close window button, debulk tissue button, and packing button), or the like.

During movement (e.g., advancement) of the catheter 20 across a lesion to remove occlusive material, manipulation of the catheter 20 by the user affects the efficiency of the cutter 28 in removing the occlusive material. For example, if a user moves the catheter 20 distally, for example, in the blood vessel too quickly, the cutting efficiency goes down because the cutter 28 makes less contact with the occlusive material than if the catheter were moved forward at a slower rate. When the catheter 20 is advanced at a slower rate, the cutter 28 makes more contact with the occlusive material and results in uniform and unfragmented cut passes. In some cases, the inefficient catheter movement is caused by the occlusive material itself (e.g., calcium). Current solutions for controlling inefficient catheter movement include training, experience, tactical feel, and visual interpretation from angiographic imaging. For example, users may be trained to advance the catheter 20 at a rate of about 2 mm/s, or to slow the advancement speed if chatter or vibration is felt. However, the current solutions rely on user implementation, and do not account for inefficient user operation.

Figure 17:
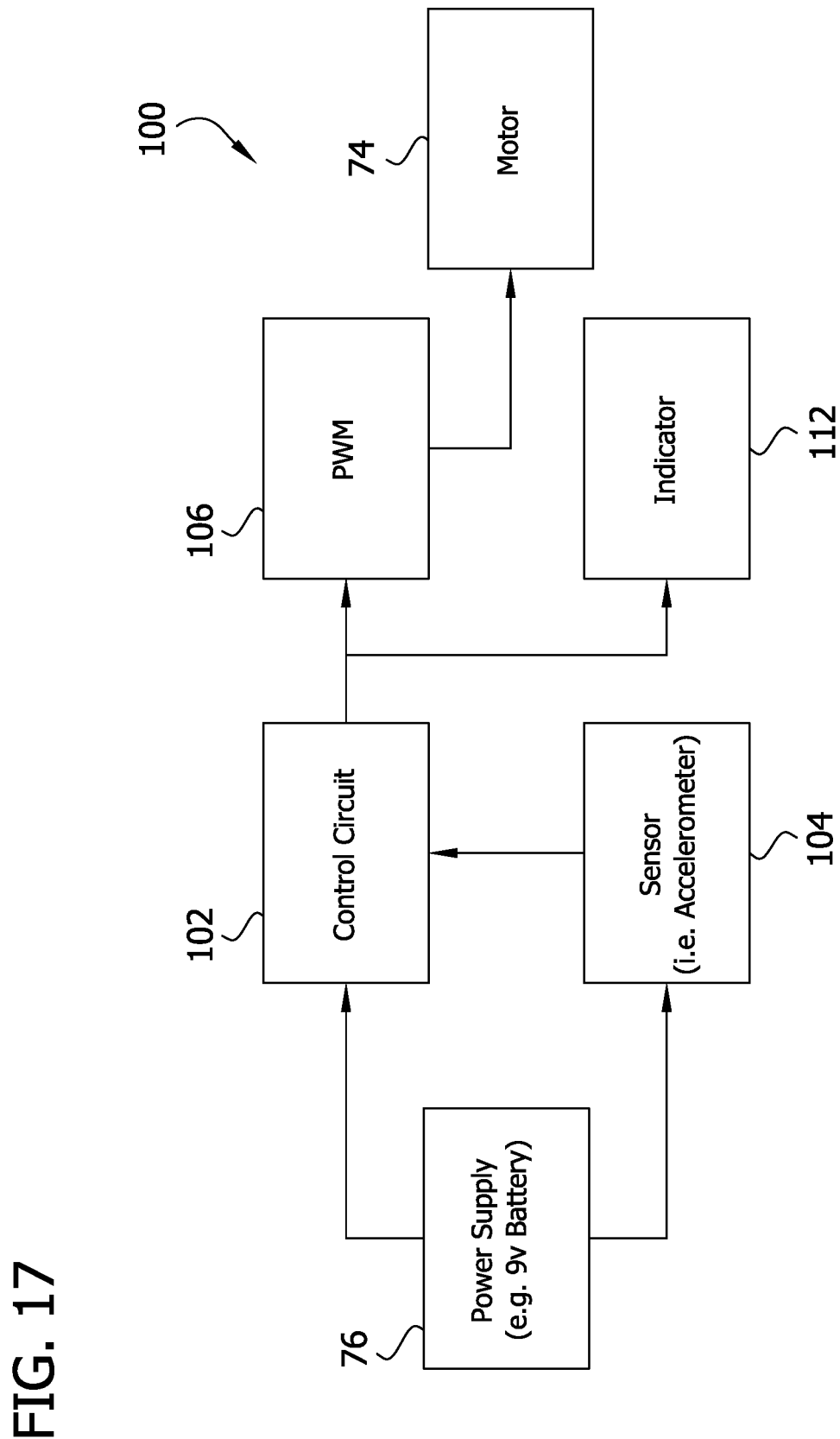
FIG. 17 is an exemplary block diagram of the operational control mechanism.
Figure 18:
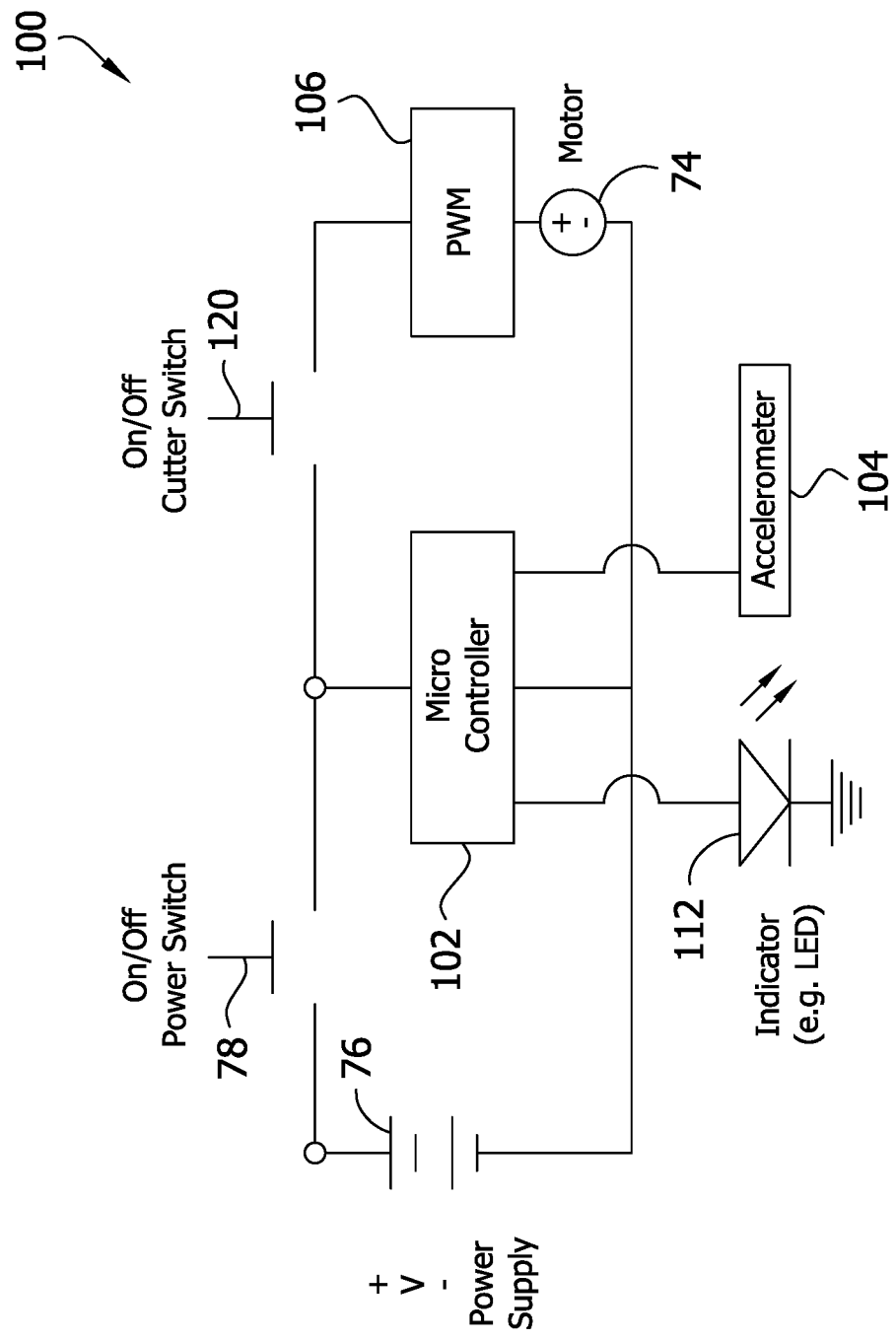
FIG. 18 is an exemplary schematic of the operational control mechanism.

As set forth above, the catheter 20 includes one or more operational control mechanisms for automatically controlling one or more operations of the catheter to increase cutting efficiency of the catheter in use. Referring to FIGS. 17 and 18, in an embodiment, the operational control mechanism comprises a motor control mechanism 100 which functions to automatically adjust the electric power (e.g., current) supplied to the cutter motor 74 from the power source 76 based on the advancement of the catheter within the body lumen during cutting operation. For example, the motor control mechanism 100 may be constructed and/or designed to detect that the catheter (e.g., the cutter 28) is advancing (e.g., moving distally) too quickly based on the rotational cut speed, or that the cutter is advancing too slowly based on the rotational cut speed (or that the rotational cut speed is faster than necessary for optimal cutting at the current advancement speed). The motor control mechanism 100 may be housed in the handle 34, as in the illustrated embodiment, or located elsewhere on the catheter 20. A block diagram of this motor control mechanism, including the motor 74, is illustrated in FIG. 17. As shown in FIG. 17, the motor control mechanism 100 includes a motor control circuit 102 and a pulse width modulation (PWM) circuit 106 connected between the power source 76 and the motor 74. In general, the motor control circuit 102 determines whether the catheter 20 is being advanced inefficiently, and the PWM circuit regulates the amount of power (i.e., current) that is supplied to the motor 74 for operating the motor and driving rotation of the cutter 28 based on the determination made by the motor control circuit 102.

Referring to FIG. 17, in an embodiment, the motor control mechanism 100 includes a sensor 104 (e.g., an accelerometer) that senses an operating parameter of the catheter 20, such as a parameter that is indicative of movement of the catheter (e.g., the advancement speed of the catheter) at some instantaneous time during the cutting operation. The sensor 104 sends a signal to the motor control circuit 102 that is indicative of the detected operating parameter (e.g., a signal indicative of the advancement speed of the catheter 20). The motor control circuit 102 determines whether the detected operating parameter is different from a threshold that equates to an optimal parameter for a given rotational cut speed, and outputs a signal to the PWM circuit 106 based on the signal it receives from the sensor 104. The PWM circuit 106 regulates the amount of power supplied to the motor 74 based on the signal it receives from the motor control circuit 102.

In one non-limiting example illustrated in FIG. 18, the motor control circuit 102 comprises a microcontroller (indicated by the same reference numeral 102) in communication with the PWM circuit 106 and with the sensor 104. The PWM circuit 106 may comprise a microcontroller that is programmed to regulate the amount of power supplied to the motor 74 by outputting a duty cycle signal to the motor based on the signal received from the microcontroller 102. It is understood that the motor control circuit 102 may comprise other types of devices, other than a microcontroller, and the PWM circuit may operate suitably without the use of a microcontroller. In the same illustrated example (or another example), the sensor 104 comprises an accelerometer for sensing changes in acceleration, vibration, and/or other motions of the catheter 20 and outputting a voltage ratio metric. The accelerometer can be positioned on the handle 34, under a distal section of the catheter body 22, or at any other suitable location. The calculated output voltage from the accelerometer is inputted to the microcontroller 102 to determine if the output voltage is different from a predetermined optimal output voltage (or outside a range of a predetermined optimal range), or if the output voltage is equal to (or within a range of) a predetermined optimal output voltage. Based on this determination, the microcontroller 102 outputs a signal that is inputted to the PWM circuit 106. The PWM circuit 106 outputs a duty cycle to the motor 74 based, at least in part, on this signal from the microcontroller 102. It is understood that sensor 104 may be of other types and configurations without departing from the scope of the present invention. Other sensors that detect a parameter of the catheter that is indicative of the movement of the catheter are within the scope of the present invention. It is also understood that a motor control circuit configured to detect a parameter of the catheter and regulate power supplied to the motor, may be of other configurations, other than illustrated and described above, without departing from the scope of the present invention.

In one non-limiting example, the motor control circuit 102 may be configured to increase the power (i.e., current) supplied to the motor 74 a predetermined amount, to thereby increase the speed of the motor if the motor control circuit determines that the catheter advancement speed is at or above a predetermined threshold advancement speed level (as determined by the sensor output, for example) for the current rotational cut speed. For example, the motor control circuit 102 may increase the speed of the motor 74 to from about 7,500 rpm to about 15,000 rpm upon making such a determination. In such an example, the predetermined threshold advancement speed level is indicative of the cutter 28 being moved inefficiently for the current rotational cut speed (e.g., advancing too quickly for optimal cutting, presence of vibration/chatter). The motor control circuit 102 increases the speed of the motor 74 to ensure the cutter 28 efficiently cuts material (e.g., with uniformity of cut depth and width of unfragmented tissue). In one non-limiting example, where the motor control circuit 102 communicates with a PWM circuit, the PWM circuit may increase the duty cycle about 50% to 100% or more from its original duty cycle to increase the speed of the motor 74.

In another non-limiting example, the motor control circuit 102 may be configured to reduce the power (i.e., current) supplied to the motor 74 a predetermined amount, to thereby decrease the speed of the motor if the motor control circuit determines that the catheter advancement speed is below a predetermined threshold advancement speed level (as determined by the sensor output, for example) for the current rotational cut speed. For example, the motor control circuit 102 may decrease the speed of the motor 74 to from about 15,000 rpm to about 7,500 rpm upon making such a determination. In such an example, the advancement speed being below the predetermined threshold advancement speed level is indicative of the cutter 28 rotating faster than necessary for optimal cutting at the current advancement speed. The motor control circuit 102 decreases the speed of the motor 74 to ensure the cutter 28 efficiently cuts material (e.g., with uniformity of cut depth and width of unfragmented tissue) while reducing fatigue of the drive system by only rotating the cutter as fast as necessary for optimal cutting. In one non-limiting example, where the motor control circuit 102 communicates with a PWM circuit, the PWM circuit may reduce the duty cycle about 100% to 50% from its original duty cycle to reduce the speed of the motor 74.

Referring to FIG. 17, the motor control mechanism 100 may include an indicator 112 (e.g., an LED) for communicating to the user that the motor control circuit 102 determined that the cutter 28 is being moved inefficiently. In one example, shown in FIG. 18, the indicator 112 (e.g., LED) is activated by the motor control circuit 102. In such an embodiment, the motor control circuit 102 may be a microcontroller. In another example, the indicator 112 may be a device that provides tactile or audible feedback to the user. Other types of indicators for communicating to the user that the cutter is being moved inefficiently do not depart from the scope of the present invention. In one embodiment, the motor control circuit 102 may activate the indicator 112 to communicate to the user when the cutter 28 is being moved efficiently and to communicate to the user when the cutter is being moved inefficiently.

In one non-limiting example, the catheter 20 may be configured to allow a user to selectively activate and deactivate the above-described operational control function of the motor control mechanism 100. For example, if the user wants to use a fixed rotational speed for the cutter 28, regardless of the advancement speed, the user can deactivate the operational control function of the motor control mechanism 100 to prevent the motor 74 from adjusting the rotational speed of the cutter based on the advancement speed of the catheter 20. In one example (FIG. 12), the handle 34 may include a switch 120 (or other input mechanism) for selectively deactivating or activating the motor control circuit 100.

Figure 19:
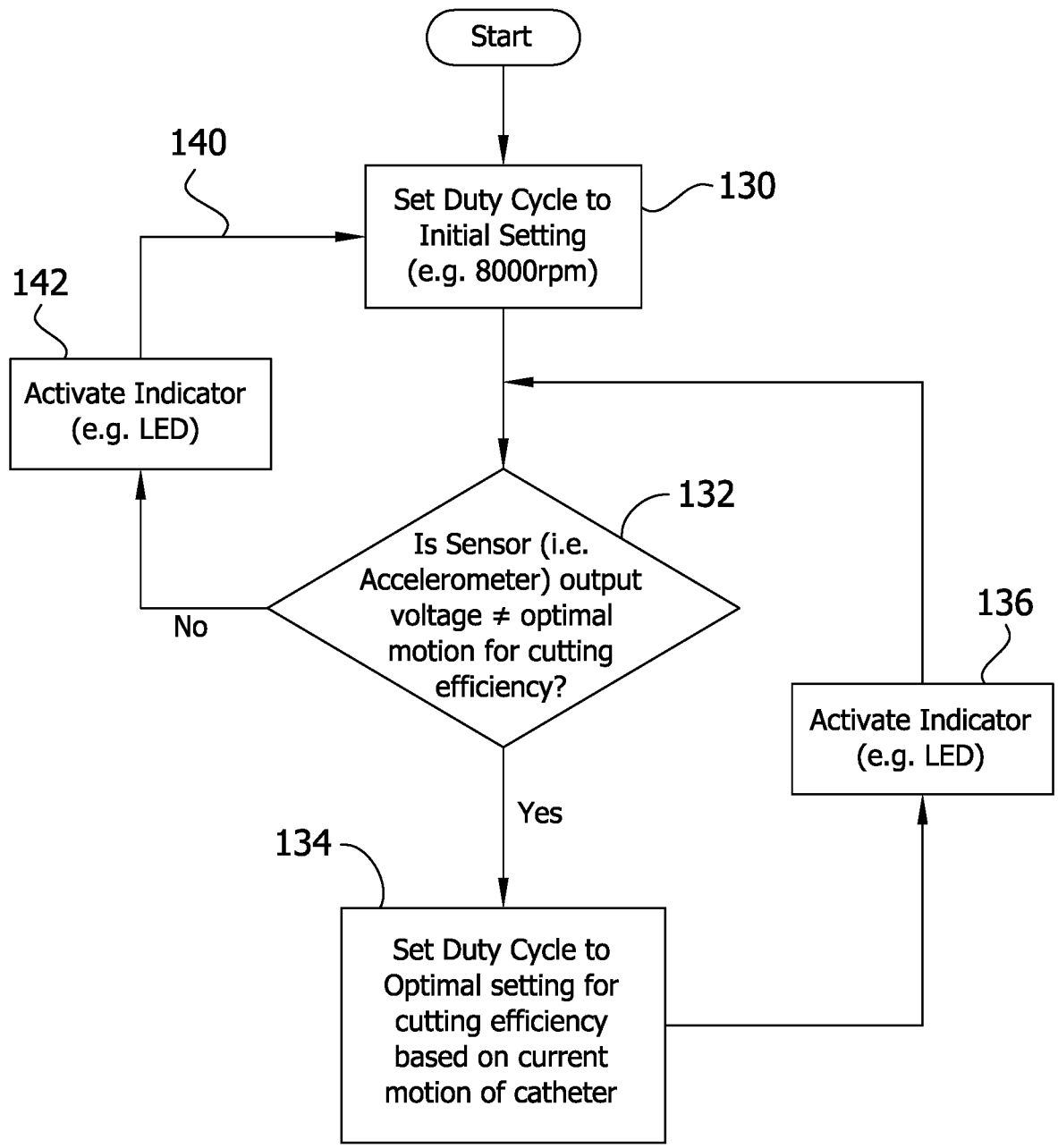
FIG. 19 is an exemplary flow diagram for a motor control circuit of the operational control mechanism.

An exemplary flow diagram for the motor control circuit 102 of the present embodiment is shown in FIG. 19. In this example, the motor control circuit 102 communicates with the PWM circuit, which includes a microcontroller for regulating the duty cycle supplied to the motor 74. When the motor control mechanism 100 is active (e.g., such as by activating the motor control mechanism using the switch 120), the microcontroller of the PWM circuit sets the duty cycle to an initial duty cycle (e.g., 8000 rpm) at step 130. At step 132, the motor control circuit 102 determines, based on the signal from the sensor 104 and during the cutting operation of the catheter 20, whether the speed of the motor 74 is optimal for cutting efficiency based on the advancement speed of the catheter. In one embodiment, the microcontroller may use computer-executable instructions for determining whether the speed of the motor 74 is optimal for cutting efficiency based on the advancement speed of the catheter. For example, in one embodiment the microcontroller stores data (e.g., a table) specifying an optimal rotational speed of the cutter 28, an optimal amount of power supplied to the motor 74, and/or an optimal rotational speed of the motor for a given catheter advancement speed. If the microcontroller 102 determines that the speed of the motor 74 is not optimal for the current advancement speed of the catheter 20 (for example, by comparing the current amount of power being supplied to the motor to the stored value of an optimal motor power for the detected advancement speed), then at step 134 the microcontroller adjusts the amount of power supplied to the motor 74 (i.e., reduces or increases the duty cycle) to adjust the speed of the motor to a level for optimal cutting efficiency at the detected advancement speed. For example, if the microcontroller determines at step 132 that the advancement speed of the catheter 20 (as calculated based on the output from the accelerometer) is too fast for the current rotational speed of the cutter 28, the microcontroller will at step 134 increase the duty cycle to increase the rotational cut speed for optimal cutting efficiency at the detected advancement speed. If, for example, the microcontroller determines at step 132 that the advancement speed of the catheter 20 (as calculated based on the output from the accelerometer) is too slow for the current rotational speed of the cutter 28, the microcontroller will at step 134 reduce the duty cycle to reduce the rotational cut speed for optimal cutting efficiency at the detected advancement speed. At step 136, the microcontroller activates the indicator 112 to communicate to the user that the cutter is being advanced inefficiently, and that the motor 74 is being (or has been) adjusted in speed based on the current advancement speed. This adjusted speed mode of the motor 74 is continued until (or unless) an advancement speed is detected by the sensor 104 that would require a further adjustment in the rotational speed of the cutter 28. If the microcontroller determines that rotational cut speed is the optimal speed for the current advancement speed of the catheter 20, then detection of advancement speed of the catheter and comparison to the predetermined optimal cutting speed for the detected advancement speed is continued at step 140, which may include a delay. Optionally, at step 142 the microcontroller activates the indicator 112 to communicate to the user that the cutter is being advanced efficiently for the current rotational cut speed. The microcontroller can also include controls for a maximum duty cycle and a stabilization time for setting the rest acceleration value. It is understood that the steps involved in determining whether the rotational cut speed is optimal for the current advancement speed and subsequently adjusting the speed of the motor 74 may be other than described above. Moreover, these steps may be performed using analog and/or digital circuits, without the use of a microcontroller.

The motor control mechanism as described above compensates for inefficient movement of the catheter 20 by adjusting the rotational speed of the cutter 28. The rotational speed of the cutter 28 is adjusted to obtain optimal cutting efficiency based on the movement (e.g., advancement speed, vibration) of the catheter 20. This allows a user to advance the catheter 20 at whatever advancement speed is comfortable while still obtaining a uniform and unfragmented cut pass. The rotational speed of the cutter is not unnecessarily increased (only when inefficiency is determined) to limit fatigue of catheter components.

The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

Embodiments of the invention may be implemented with computer-executable instructions. The computer-executable instructions may be organized into one or more computer-executable components or modules. Aspects of the invention may be implemented with any number and organization of such components or modules. For example, aspects of the invention are not limited to the specific computer-executable instructions or the specific components or modules illustrated in the figures and described herein. Other embodiments of the invention may include different computer-executable instructions or components having more or less functionality than illustrated and described herein.

Having described the invention in detail, it will be apparent that modifications and variations are possible without departing from the scope of the invention defined in the appended claims. When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. In view of the above, it will be seen that the several objects of the invention are achieved and other advantageous results attained.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A tissue-removing catheter for removing tissue from a body lumen during a tissue-removing operation thereof, the tissue-removing catheter comprising:
    an elongate catheter body configured for insertion into the body lumen, the catheter body having opposite distal and proximal portions, and a longitudinal axis extending between the distal and proximal portions;
    a tissue-removing element located generally at the distal portion of the catheter body and configured to rotate generally about a rotational axis;
    an electric motor operably connected to the tissue-removing element to impart rotation of the tissue-removing element about the rotational axis during the tissue-removing operation of the catheter;
    a sensor configured to detect a linear advancement speed of the catheter body during the tissue-removing operation of the catheter;
    an indicator;
    a motor control circuit in electrical communication with the sensor, the motor, and the indicator, wherein during an operational control function, the motor control circuit is configured to:
        receive a signal from the sensor of the detected linear advancement speed of the catheter body in the body lumen during the tissue-removing operation of the catheter,
        determine whether the received signal is indicative of the detected linear advancement speed of the catheter body being greater than a predetermined threshold linear advancement speed based on a rotational speed of the tissue-removing element,
        activate the indicator if the received signal is indicative of the detected linear advancement speed of the tissue-removing element being greater than the predetermined threshold linear advancement speed,
        enable electrical power to be supplied to the motor to enable rotation of the tissue-removing element about the rotational axis if the advancement speed detected by the sensor is greater than the predetermined threshold linear advancement speed, and
        increase the amount of electrical power supplied to the motor to increase the rotational speed of the tissue-removing element if the advancement speed detected by the sensor is greater than the predetermined threshold linear advancement speed.

2. The tissue-removing catheter set forth in claim 1, wherein the sensor comprises an accelerometer.

3. The tissue-removing catheter set forth in claim 1, wherein the motor control circuit comprises a microcontroller.

4. The tissue-removing catheter set forth in claim 1, further comprising a handle connected to the proximal portion of the catheter body, wherein the motor control circuit and the motor are disposed in the handle.

5. The tissue-removing catheter set forth in claim 4, wherein the sensor is disposed in the handle.

6. The tissue-removing catheter set forth in claim 4, wherein the sensor is disposed in the distal portion of the catheter body.

7. The tissue-removing catheter as set forth in claim 1, further comprising a pulse width modulation (PWM) circuit configured to increase the amount of electrical power supplied to the motor, wherein the motor control circuit is in electrical communication with the PWM circuit.

8. A tissue-removing catheter for removing tissue from a body lumen during a tissue-removing operation thereof, the tissue-removing catheter comprising:
    an elongate catheter body configured for insertion into the body lumen, the catheter body having opposite distal and proximal portions, and a longitudinal axis extending between the distal and proximal portions;
    a tissue-removing element located generally at the distal portion of the catheter body and configured to rotate generally about a rotational axis;
    an electric motor operably connected to the tissue-removing element to impart rotation of the tissue-removing element about the rotational axis during the tissue-removing operation of the catheter;
    a sensor configured to detect vibration of the catheter body in the body lumen during the tissue-removing operation of the catheter; and a motor control circuit in electrical communication with the sensor and the motor, wherein during an operational control function, the motor control circuit is configured to:
- receive, from the sensor, a signal indicative of the detected vibration of the catheter body in the body lumen during the tissue-removing operation of the catheter,
- determine whether the received signal is indicative of the detected vibration of the catheter body being greater than a predetermined threshold amount of vibration based on a rotational speed of the tissue-removing element,
- if the received signal is indicative of the detected vibration of the catheter body being greater than the predetermined threshold amount of vibration, at least one of (i) generate an indicator control signal for activating an indicator and (ii) adjust the rotational speed of the tissue-removing element, and
- increase the rotational speed of the tissue-removing element if the received signal is indicative of the detected vibration of the catheter body being greater than the predetermined threshold amount of vibration.

9. The tissue-removing catheter set forth in claim 8, wherein the motor control circuit is configured to increase the rotational speed of the tissue-removing element by increasing the amount of electrical power supplied to the motor.

10. The tissue-removing catheter as set forth in claim 9, further comprising a pulse width modulation (PWM) circuit configured to increase the amount of electrical power supplied to the motor, wherein the motor control circuit is in electrical communication with the PWM circuit.

11. The tissue-removing catheter set forth in claim 8, wherein the sensor comprises an accelerometer.

12. The tissue-removing catheter set forth in claim 8, wherein the motor control circuit comprises a microcontroller.

13. The tissue-removing catheter set forth in claim 8, further comprising a handle connected to the proximal portion of the catheter body, wherein the motor control circuit and the motor are disposed in the handle.

14. The tissue-removing catheter set forth in claim 13, wherein the sensor is disposed in the handle.

15. The tissue-removing catheter set forth in claim 13, wherein the sensor is disposed in the distal portion of the catheter body.

16. The tissue-removing catheter set forth in claim 8, wherein the tissue-removing catheter includes the indicator and the indicator is in electrical communication with the motor control circuit.

17. The tissue-removing catheter set forth in claim 16, wherein the motor control circuit is configured to activate the indicator if the received signal is indicative of the detected vibration of the catheter body being greater than the predetermined threshold amount of vibration.

18. A tissue-removing catheter for removing tissue from a body lumen during a tissue-removing operation thereof, the tissue-removing catheter comprising:
- an elongate catheter body configured for insertion into the body lumen, the catheter body having opposite distal and proximal portions, and a longitudinal axis extending between the distal and proximal portions;
- a tissue-removing element located generally at the distal portion of the catheter body and configured to rotate generally about a rotational axis;
- an electric motor operably connected to the tissue-removing element to impart rotation of the tissue-removing element about the rotational axis during the tissue-removing operation of the catheter;
- a sensor configured to detect a linear advancement speed of the catheter body during the tissue-removing operation of the catheter;
- an indicator; and
- a motor control circuit in electrical communication with the sensor, the motor, and the indicator, wherein during an operational control function, the motor control circuit is configured to:
  - receive a signal from the sensor of the detected linear advancement speed of the catheter body in the body lumen during the tissue-removing operation of the catheter,
  - determine whether the received signal is indicative of the detected linear advancement speed of the catheter body being greater than a predetermined threshold linear advancement speed based on a rotational speed of the tissue-removing element,
  - activate the indicator if the received signal is indicative of the detected linear advancement speed of the tissue-removing element being greater than the predetermined threshold linear advancement speed, and
  - increase the amount of electrical power supplied to the motor to increase the rotational speed of the tissue-removing element if the advancement speed detected by the sensor is greater than the predetermined threshold linear advancement speed.

* * * * *